(12) United States Patent
Santo et al.

(10) Patent No.: US 7,572,469 B2
(45) Date of Patent: Aug. 11, 2009

(54) THERAPEUTIC LOTION FOR DERMATITIS

(75) Inventors: Tetsuo Santo, 360-130, Hinashicho, Hamada-Shi, Shimane 697-1322 (JP); Songhua Li, Izumo (JP); Ruwei Wang, Zhejiangsheng (CN); Sumio Iwasaki, Izumo (JP)

(73) Assignee: Tetsuo Santo, Shimane (JP)

( * ) Notice: Subject to any disclaimer, the term of this patent is extended or adjusted under 35 U.S.C. 154(b) by 62 days.

(21) Appl. No.: 10/511,017

(22) PCT Filed: Apr. 15, 2002

(86) PCT No.: PCT/JP02/03746

§ 371 (c)(1), (2), (4) Date: Jun. 27, 2005

(87) PCT Pub. No.: WO03/086432

PCT Pub. Date: Oct. 23, 2003

(65) Prior Publication Data

US 2005/0260289 A1    Nov. 24, 2005

(51) Int. Cl.
*A61K 36/906* (2006.01)

(52) U.S. Cl. ...................................... 424/756

(58) Field of Classification Search ................. None
See application file for complete search history.

(56) References Cited

U.S. PATENT DOCUMENTS 5,229,130 A    7/1993   Sharma et al.
5,716,800 A *  2/1998   Meybeck et al. .............. 435/52

(Continued)

FOREIGN PATENT DOCUMENTS

DE           19838462       3/2000

(Continued)

OTHER PUBLICATIONS

Article Titled "Flavonoid Aglycons in Foods of Plant Origin II. Fresh and Dried Fruits" jointly authored by Lugasi et al., in Acta Alimentaria, Mar. of 2002, vol. 31, No. 1, (pp. 63-71).

(Continued)

*Primary Examiner*—Christopher R. Tate
*Assistant Examiner*—Deborah A. Davis
(74) *Attorney, Agent, or Firm*—J.C. Patents

(57) ABSTRACT

TECHNICAL FIELD: Lotion for therapy of dermatitis
TECHNICAL PROBLEM: To provide a lotion for therapy effective against atopic dermatitis.
MEANS FOR SOLVING: It has a composition: Lightyellow Sophora Root, 3%; Turmeric, 2%; Magnolia Bark, 2%; Moutan Bark, 2%; Isatis Leaf, 1%; Borneo Camphor Tree (*Dryobalanops aromatica* Gaertn.f.), 1%; Amur Cork Tree, 2%; Angelicae Dahuricae Root, 1%; Lemon, 3%; Smartweed, 2%; Licorice, 0.5%; Cnidii Rhizoma, 0.5%; Japanese Angelica Root, 0.5%; salicylic acid, 0.5%; resorcinol, 0.5%; alcohol, 30%; and water, 48.5%.

A significant therapeutic effect against atopic dermatitis is obtained by a synergistic effect between antibacterial, antiviral, antiallergic, antiphlogistic, and blood-circulation accelerating actions as pharmacological effects of Lightyellow Sophora Root, Turmeric, Magnolia Bark, Moutan Bark, Isatis Leaf, Borneo Camphor Tree (*Dryobalanops aromatica* Gaertn.f.), Amur Cork Tree, Angelicae Dahurikae Root, Lemon, Smartweed, and Licorice, accelerating action for skin permeation and antifungal-sterilizing action of Cnidii Rhizoma and Japanese Angelicae Root, accelerating action for keratinization and antifungal-sterilizing action of salicylic acid and resorcinol, as described above.

Principal Use: It is used for the therapy of dermatitis, particularly of atopic dermatitis.

4 Claims, 7 Drawing Sheets

(A)

(B)

U.S. PATENT DOCUMENTS

| | | | |
|---|---|---|---|
| 5,753,256 | A | 5/1998 | Cordes et al. |
| 6,309,575 | B1 * | 10/2001 | Boutin et al. ............... 264/161 |
| 6,375,961 | B1 * | 4/2002 | Carson et al. ............... 424/401 |
| 2003/0108628 | A1 * | 6/2003 | Babish et al. ............... 424/756 |
| 2004/0185123 | A1 * | 9/2004 | Mazzio et al. ............... 424/730 |

FOREIGN PATENT DOCUMENTS

| | | |
|---|---|---|
| EP | 0308210 | 3/1989 |
| JP | 60-087224 | 5/1985 |
| JP | 63-022506 | 1/1988 |
| JP | 4-082830 | 3/1992 |
| JP | 4-356423 | 12/1992 |
| JP | 4-356424 | 12/1992 |
| JP | 5-043449 | 2/1993 |
| JP | 6-087732 | 3/1994 |
| JP | 6-211673 | 8/1994 |
| JP | 6-211713 | 8/1994 |
| JP | 6-279305 | 10/1994 |
| JP | 7-138173 | 5/1995 |
| JP | 7-145035 | 6/1995 |
| JP | 7-309713 | 11/1995 |
| JP | 8-081375 | 3/1996 |
| JP | 9-030931 | 2/1997 |
| JP | 9-087189 | 3/1997 |
| JP | 9-124500 | 5/1997 |
| JP | 10-152433 | 6/1998 |
| JP | 10-226639 | 8/1998 |
| JP | 2000-044481 | 2/2000 |
| JP | 2000-169383 | 6/2000 |
| JP | 2000-239178 | 9/2000 |
| JP | 2001-226213 | 8/2001 |
| JP | 2002-047193 | 2/2002 |
| JP | 2002-053485 | 2/2002 |
| WO | WO 98/40086 | 9/1998 |
| WO | WO 00/59520 | 10/2000 |

OTHER PUBLICATIONS

Article Titled "Tea of *Isatis tinctoria* (woad) responses by allergic patients in vivo and in vitro" jointly authored by Diel F. et al., in Aktuelle Emahrungsmedizin Klinik und Praxis, 1992, vol. 17, No. 1 (pp. 34-36).

Article Titled "Histamine-Release Effectors from *Angelica dahurica* var. *dahurica* Root" jointly authored by Kimura Y. et al., in J. Nat. Prod., 1997, Vo. 60. No. 3, (pp. 249-251).

Article Titled "Antiallergic activity of Extracts from *Curcuma longa* (4): Effect of Curcuminoids on Release of Inflammatory Mediators and Experimental Model for Atopic Dermatitis" jointly authored by Yano, et al., in J Tradit Med, 1997, vol. 14, No. 4, (pp. 430-431).

Article Titled "Antiallergic activity of *Curcuma longa*: Active principles and mode of action" jointly authored by Yano et al., in J Tradit Med, 1995, vol. 12, No. 4, (pp. 269-272).

* cited by examiner (A)

(B)

(A)

(B)

THERAPEUTIC LOTION FOR DERMATITIS

TECHNICAL FIELD

The present invention relates to a lotion for therapy of dermatitis, and relates to a lotion for therapy of dermatitis which is suitable to treat various dermatitis including eczema, particularly, for example, atopic dermatitis.

BACKGROUND ART

Patients having dermatitis, particularly patients having atopic dermatitis, have suddenly increased in recent years. While the grounds for the sudden increase of patients having atopic dermatitis has yet not been sufficiently clarified, it is considered that the grounds are classified into three large groups.

The first ground is a change in the eating habit. That is, by an increase in consumption of meat as well as dairy product such as butter, cheese and the like, changed from the conventional vegetable-centered diet, it is considered that the physical constitution itself has been changed.

The second ground is a change in the living environment. That is, by a change from the conventional houses using wood, plaster, paper, rush-mat and the like to houses using various synthetic building materials, chemically synthesized size, chemical mat and the like, it is considered that various chemical substances contained in these building materials are released in the living environment resulting in the change in the physical constitution. In addition, irritation on the skin may be increased by a change from the conventional clothes made of natural material fibers such as wool, cotton and the like to clothes made of various chemical fibers resulting in increase of irritation onto the skin. A change from washing with soaps to washing with synthetic detergents and dry-cleaning, and a use of shampoos, rinses, hair conditioners may also be grounds.

As the third ground, it is considered that a level down in immunity is caused by speed-up in the rhythm of life and raised level of work proceeded in all the aspect, resulting in exposure of infants and adults to excess stresses.

Atopic dermatitis is a disease occurred at from two- or three-months old to about ten years old when resistance power is poor and is known to be a disease accompanied by intense itch with wetting and erosion; the itch is characterized in that it gives a mental pain to the patients and aggravates symptoms by scratching; particularly, in the case of infant patients, it is painful not only for the patients themselves but also for parents and near relations.

Although various countermeasures have been examined and practiced for the prophylaxis or therapy of this atopic dermatitis, most of them are countermeasures belonging to the symptomatic therapy; particularly known are antihistaminic agents, antiallergic agents, antiphlogistic agents, steroidal agents and the like for the symptomatic therapy of western medicine, but all of them have been unsatisfactory in pharmacological effect and side effects.

For example, although antihistaminic agents and antiallergic agents have an action of suppressing itch, they have problems in the duration of effect and antiphlogistic effect, and are problematic in long-term administration for chronic itching because sometimes they bring about troubles in the daily life due to symptoms such as weariness, sleepiness and the like caused by administration.

Although steroidal agents have generally a high pharmacological effect, they are fundamentally drugs for suppressing symptoms, and sometimes the cure cannot be attained even by a long-term administration of steroidal agents; they are problematic because of their strong drug-characteristic side effects; for example, sometimes they cause dermatrophia in which the skin becomes thin like a flimsy, capillarectasia in which capillary blood vessel in the skin rises forming red-skin, and various infections such as fungal infection, folliculitis (pimple), herpes and the like due to decrease in the immune power. Additionally, when a very large amount of a very strong steroidal agent is used within a short period, sometimes functional disorder of adrenal grand, shock and the like occurs. In another case, when use of steroidal agent is suddenly discontinued after a long-term use, problems arises that the daily life become difficult by a revival of symptoms suppressed before by the steroidal agent and a rebound phenomenon (jump back) in which symptoms such as itching, redness, swelling and the like increases more than before.

In addition, based on the fact that *staphylococcus aureus* and others were found in the diseased part of atopic dermatitis, application of Isodine, a disinfectant agent, has been practiced in some cases. Indeed the effect of application of Isodine has been confirmed in a skin on which bacteria is abundant, isodine is effective only to bacteria floating on the surface of skin, and has no effect against bacteria within a biological membrane or bacteria invaded deeply in the skin. Not only that, Isodine is liable to cause a rash, and when once a rash is caused, the reaction is repeated and sometimes an ulcer is formed on the skin or a reaction such as shock or the like is caused. Moreover, sometimes hypothyroidism is induced.

From a similar viewpoint against bacteria, sometimes super acidic water is used, but problems similar to those in Isodine arise.

In addition to the above-described countermeasures based on western medicine, treatments by Sino-Japanese medicament have also been practiced. For example, respective crude drug ingredients of Rhizoma coptidis detoxication soup and Heat-clearing and wind-dispelling powder as therapeutic agents for atopic dermatitis are Baikal skullcap, Coptis Root, Gardenia Fruit, Amur Cork Tree and Japanese Angelicae Root, Chinese Fox-Glove Root, Gypsum, Saposhnikoviae Radix, Great Burdock Achene, Akebiae Stem, *Anemarrhena* Rhizome, Sesame, *Cryptotympana atrata*, Lightyellow Sophora Root; since they belong to anti-itching agents for suppressing itch or blood-activation agents for stopping pain by improving blood circulation and therefore respective drugs belong to the symptomatic therapy dealing with individual symptoms, these medicaments cannot be said to be medicaments for fundamental cure.

In addition, although drugs for paint such as ointments containing Sino-Japanese drugs have been prepared, these belong also to so-called symptomatic therapy and therefore are far from the fundamental cure by improvement of physical constitution.

Moreover, while the activity is mild, Sino-Japanese drugs with a purpose of suppressing the aforementioned side effects have been proposed. For example, Japanese Patent Publication JP-A-6-166629 has proposed an agent for improving atopic dermatitis formed by mixing Potent Bupleuri Decoction and *Angelica* peony powder. Indeed side effects are suppressed in these agents for improving atopic dermatitis, there is a problem that its anti-itching effect is not sufficient.

Beside, Japanese Patent Publication JP-A-8-301779 has proposed an external drug for atopic dermatitis containing as an active ingredient an extract solution from one, two or more plants selected from the group consisting of Linden, Lemonbalm, Fenugreek, Borage, *Ligusticum chuanxiong* Hort, Pink Pyrola, Willowleaf Swallowwort Rhizome, *Clerodendron cyrtophyllum*, and *Clinopodium chinense*.

However, while the ointment for atopic dermatitis exerts some anti-itching effect and disease-improving effect by applying it onto the diseased part, a problem arises that the skin is liable to sweat due to obstruction to skin respiration by coating layer, and moreover, sometimes itching increases because the diseased part becomes wet condition due to obstruction of evaporation and emanation of the perspired sweat by the coating layer Therefore, the purpose of the present invention is to provide a lotion for therapy of dermatitis which is not an external preparation such as an ointment like conventional ones as described above, which enables therapy of atopic dermatitis, and which is a liquid form.

DISCLOSURE OF THE INVENTION

The lotion for therapy of dermatitis according to the present invention is characterized in that it contains extracts drawn from one, two or more plants selected from the group consisting of Lightyellow Sophora Root, Turmeric, Magnolia Bark, Moutan Bark, Isatis Leaf, and Borneo Camphor Tree (claim 1).

The families, main components and principal activities of the plants as raw materials for the above-mentioned respective extracts drawn from plants are described in the following:

(1) Lightyellow Sophora Root (Kujin) (*Sophora flavescens* Ait.)
Plant family: Leguminosae plant fravescens
Main components: Matorine, Kurarinore
Principal activities: Antibacterial, Antiviral, Antiallergic (2) Turmeric (Ukon) (*Curcuma aromatica* Salisb.)
Plant family: Zingiberacea Plant
Main components: Curcumol, Curdion
Principal activities: Antibacterial, Antiphlogistic, Blood-circulation improving (3) Magnolia Bark (Kouboku) (*Magnolia officinalis* Rehd. et Wils.)
Plant family: Magnoliaceae plant
Main components: Honoriol, β-eudesml
Principal activities: Antibacterial, Antiphlogistic (4) Moutan Bark (Botanpi) (*Paeonia suffruticosa* Andr.)
Plant family: Paeoniaceae plant
Main components: Paeonol, Benzoic acid, Phytosuterol
Principal activities: Antiphlogistic, Blood-circulation improving (5) Isatis Leaf (Taiseiyou) (*Isatis tinctoria* L.)
Plant family: Acantaceae plant
Main components: Indigo, Indirubin, Idican, Tace Element
Principal activities: Antibacterial, Antiviral, Antiallergic In addition, Isatis Leafs prepared from *Baphicacanthus cusia* Bremek, Isatis Indigotica Eort, *Polygonum tinctorium* Ait., *Clerodendron cyrtophyllum* Turcz. and the like can be used.

(6) Borneo Camphor Tree (Hyouhen) (*Dryobalanops aromatica* Gaertn.f.)
Plant family: Diptercarpaceae plant. Crystals prepared by processing resin from *Dipterocarpus retusus*.
Main components: Volatile oil, α-Borneol
Principal activities: Antibacterial, Antiphlogistic, Anti-itching According to the above described lotion for therapy of dermatitis, curing potential is elevated by antibacterial, antiviral, antiphlogistic, blood-circulation improving and other effects together with a depression effect against allergens, and thus therapeutic effects against atopic dermatitis can be enhanced, owing to antibacterial effect of Lightyellow Sophora Root, Turmeric, Magnolia Bark, Isatis Leaf, and Borneo Camphor Tree (*Dryobalanops aromatica* Gaertn.f.), antiviral and antiallergic effects of Lightyellow Sophora Root and Isatis Leaf, antiphlogistic effect of Turmeric, Magnolia Bark, Moutan Bark and Borneo Camphor Tree (*Dryobalanops aromatics* Gaertn.f.), blood-circulation improving effect of Turmeric and Moutan Bark, anti-itching effect of Borneo Camphor Tree (*Dryobalanops aromatica* Gaertn.f.), or by a synergistic effect of them.

The invention is also characterized in that an auxiliary agent is added to the above described extracts drawn from plants (claim 2).

As the auxiliary agent, materials having various auxiliary activities can be adopted, including one for assistance and enhancement of pharmacological effects, namely antibacterial, antiviral, antiallergic, antiphlogistic, blood-circulation and anti-itching effects, of aforementioned extracts drawn from plants, one for addition of pharmacological effects, for example, antifungal, sterilizing effects and others, which are lacking in aforementioned extracts drawn from plants, one for improvement of easiness of applying as a liquid lotion by dissolving the aforementioned extracts drawn from plants, one for accelerating skin permeation so that the pharmacologically active ingredients applied onto the diseased part permeate deeply into inside of the skin, or further, one for accelerating keratinization of skin already cured by the effects of the pharmacologically active ingredients applied onto the diseased part, and so on.

According to the above lotion for therapy of dermatitis, with the auxiliary agent, the therapeutic effect is promoted by assisting or enhancing the pharmacological effects of the extracts drawn from plants namely Lightyellow Sophora Root, Turmeric, Magnolia Bark, Moutan Bark, Isatis Leaf, and Borneo Camphor Tree (*Dryobalanops aromatica* Gaertn.f.), by adding a pharmacological effect lacking in the above described extracts drawn from plants, by improving easiness of applying as a lotion, or further, by accelerating effect of skin permeation and acceleration effect of keratinization, and inconvenience such as side effects occurred by use continued for a period needed in therapy and the like can be avoided.

The invention is also characterized in that the auxiliary agent includes an auxiliary extract drawn from a medicinal herb, accelerator for skin permeation, accelerator for keratinization, alcohol and water (claim 3).

According to the above lotion for therapy of dermatitis, with the auxiliary extract drawn from a medicinal herb, the therapeutic effect is promoted by assisting or enhancing the pharmacological effects of the extracts drawn from plants namely Lightyellow Sophora Root, Turmeric, Magnolia Bark, Moutan Bark, Isatis Leaf, and Borneo Camphor Tree (*Dryobalanops aromatica* Gaertn.f.), by adding a pharmacological effect as described above lacking in the above described extracts drawn from plants, by improving easiness of applying as a lotion, and additionally, by accelerating agent for skin permeation acting for permeation of the pharmacologically active ingredients deeply under the skin of diseased part, and further, by accelerating agent for keratinization of skin acting for keratinization of the diseased part so that the metabolism in the diseased part is elevated. Besides, alcohol acts for easiness of dissolving respective ingredients, and for imparting cold feeling on applying, and furthermore, is useful for effective therapy by remaining the pharmacologically active ingredients on the diseased part by evaporation after applying; water acts for easiness of applying onto the diseased part by decreasing viscosity as a lotion, and is useful for effective therapy by remaining the pharmacologically active ingredients on the diseased part by evaporation after applying.

The invention is also characterized in that the above described auxiliary extract drawn from a medicinal herb contains extracts drawn from one, two or more selected from the group of Amur Cork Tree, Angelicae Dahurikae Root, Lemon, Smartweed and Licorice (claim 4).

The families, main components and principal activities of the medicinal herb as a raw material for the auxiliary extract drawn from a medicinal herb are described briefly in the following:

(1) Amur Cork Tree (Oubaku) (*Phellodendron amurense* Rupr.)
Plant family: Rutaceae plant
Main components: Berberine, Phellodendorine
Principal activity: Antibacterial, Antiphlogistic (2) Angelicae Dahuricae Root (Hakusi) (*Angelica dahurica* Benth. et Hook.)
Plant family: Umbelliferae plant
Main components: Byak-anngelicin, Imperatorin
Principal activities: Antibacterial, Antiphlogistic, Antiallergic (3) Lemon (Lemon)
Plant family: Rutaceae plant, Food Additive
Main component: Lemon acid
Principal activities: Antiallergic (4) Smartweed (Kojou) (*Polygonum cuspidatum* sieb. et Zicc.)
Plant family: Polygonaceae plant (Smartweed Plant)
Main components: Glycosides, Flabonoids
Principal activities: Antibacterial, Antiviral, Antiallergic (5) Licorice (Kanzou) (*Glycyrrhiza uralensis* Fisch.)
Plant family: Legminosae plant
Main components: Glycyrrhetic acid, Flabonoids
Principal activities: Antiallergic, Antiphlogistic According to the above lotion for therapy of dermatitis, the antibacterial, antiviral, antiallergic, antiphlogistic, blood-circulation improving and anti-itching effects of Lightyellow Sophora Root, Turmeric, Magnolia Bark, Moutan Bark, Isatis Leaf and Borneo Camphor Tree (*Dryobalanops aromatica* Gaertn.f.) can be assisted and enhanced by antibacterial activity of Amur Cork Tree, Angelicae Dahurikae Root and Smartweed, antiviral activity of Smartweed, antiallergic activity of Angelicae Dahurikae Root, Lemon, Smartweed and Licorice, and antiphlogistic activity of Amur Cork Tree, Angelicae Dahurikae Root and Licorice, which are auxiliary extracts drawn from medicinal herbs The invention is also characterized in that the above described accelerating agent for skin permeation contains one, two or more selected from the group of Cnidii Rhizoma, Japanese Angelicae Root and dimethylsulfoxide (claim 5).

The families, main components and principal activities of Cnidii Rhizoma and Japanese Angelicae Root, and properties and principal activities of dimethylsulfoxide are described in the following:

(1) Cnidii Rhizoma (Senkyu) (*Ligusticum chuanxiong* lort)
Plant family: Umbelliferae plant
Main components: Volatile oil, Tetramethylpyrazine, Senkyunolide, Ferulic acid
Principal activities: Skin permeation accelerating, Blood-circulation accelerating, Sedative, Antispasmodic (2) Japanese Angelicae Root (Touki) (*Angelica sinensis* (Olive) Diels.)
Plant family: Umbelliferae plant
Main components: Volatile oil, Ferulic acid, Vitamin E, Vitamin A, Vitamin $B_{12}$ Principal activities: Skin permeation accelerating, Blood-circulation accelerating, Anemia improving, Immunity regulating, Antiallergic (3) Dimethylsulfoxide
Properties: Soluble in alcohol and water
Principal activity: Skin permeation accelerating According to the above lotion for therapy of dermatitis, the therapeutic effect can be elevated not only at the surface of skin but also in deep tissue of skin by permeating and penetrating effectively and deeply the pharmacologically active ingredients of the extracts drawn from plants into the subcutaneous tissue by the skin permeation accelerating action of Cnidii Rhizoma, Japanese Angelicae Root and dimethylsulfoxide, and moreover, the therapeutic effect can be elevated by blood-circulation accelerating, sedative and antispasmodic action of Cnidii Rhizoma, as well as blood-circulation accelerating, anemia improving, immunity regulating and antiallergic action of Japanese Angelicae Root.

The invention is also characterized in that the above described accelerating agent for keratinization contains one or two selected from the group of salicylic acid and resorcinol (claim 6).

The properties and principal activities of salicylic acid and resorcinol are described briefly in the following:

(1) Salicylic acid (*Acidurn Salicylicum*)
Properties: Easily soluble in alcohol, soluble in water
Principal activities: Keratinization accelerating, Antiseptic (2) Resorcinol
Properties: Soluble in alcohol and water
Principal activities: Keratinization accelerating, Antiseptic, Antipruritic, Antimold According to the above described lotion for therapy of dermatitis, a lotion having a higher therapeutic effect can be obtained by accelerating metabolism in the diseased part by keratinization accelerating action of salicylic acid and/or resorcinol together with a therapeutic effect given by the therapeutically active ingredients in the extracts drawn from plants and auxiliary agents onto the diseased part.

The invention is also characterized in that the volume ratios of the extracts drawn from plants:accelerating agent for skin permeation:accelerating agent for keratinization in the above mentioned auxiliary agent is 53 to 89%:8 to 38%:6 to 10% (claim 7).

When the extracts drawn from plants is less than 53%, appearance of medical effect is slow or no improving effect appears; when it exceeds 89%, there is a fear that a side effect in which skin become red and swelled or the symptom become worse occurs. When accelerating agent for skin permeation is less than 8%, skin permeation accelerating action is insufficient; when it exceeds 38%, there is a fear that a side effect in which skin become red and swelled or the symptom become worse occurs. When accelerating agent for keratinization is less than 6%, keratinization accelerating action is insufficient; when it exceeds 10%, there is a fear that a side effect in which skin become red and swelled or the symptom become worse occurs.

According to the above described lotion for therapy of dermatitis, the extracts drawn from plants, accelerating agent for skin permeation and accelerating agent for keratinization are contained with a good balance, and a lotion having a high therapeutic effect and having a suppressed excess irritation by applying can be obtained.

The invention is also characterized in that the volume ratios of respective ingredients are Lightyellow Sophora Root, 2.7 to 3.3%; Turmeric, 1.8 to 2.2%; Magnolia Bark, 1.8 to 3.3%; Moutan Bark, 1.8 to 3.3%; Isatis Leaf, 0.9 to 1.1%; Borneo Camphor Tree (*Dryobalanops aromatics* Gaert-n.f), 0.9 to 1.1%; Amur Cork Free, 1.8 to 2.2%; Angelicae Dahuricae Root, 0.9 to 1.1%; Lemon, 0 to 3.3%; Smartweed, 0 to 2.2%; Licorice, 0 to 1%; Cnidii Rhizoma, 0.45 to 0.55%; Japanese *Angelica* Root, 0 to 0.55%; salicylic acid, 0.45 to 0.55%; resorcinol, 0.45 to 0.55%; alcohol, 25 to 35%; and water, 45 to 51% (claim 8).

When respective ingredients other than alcohol and water among the above described ingredients are less than the lower limit of the above range, appearance of medical effect is slow or no medical effect appears; when it exceeds the upper limit of the above range, there is a fear that a side effect in which skin become red and swelled or the symptom become worse occurs.

According to the above described lotion for therapy of dermatitis, a high therapeutic effect against atopic dermatitis can be obtained owing to the fact that well-balanced antibacterial, antiviral, antiallergic, antiphlogistic, blood-circulation accelerating and anti-itching effects of Lightyellow Sophora Root, Turmeric, Magnolia Bark, Moutan Bark, Isatis Leaf and Borneo Camphor Tree (*Dryobalanops aromatica* Gaertn.f.) as the main extracts drawn from plants, assisting action and enhancing action for pharmacological activities by Amur Cork Tree, Angelicae Dahurikae Root, Lemon, Smartweed, Licorice and the like as the auxiliary extracts drawn from plants, skin permeating action of Cnidii Rhizoma and/or Japanese Angelicae Root, and keratinization accelerating action of salicylic acid and/or resorcinol are obtained.

The invention is also characterized in that the volume ratios of respective ingredients are Lightyellow Sophora Root, 3%; Turmeric, 2%; Magnolia Bark, 2%; Moutan Bark, 2%; Isatis Leaf, 1%; Borneo Camphor Tree (*Dryobalanops aromatica* Gaertn.f.), 1%; Amur Cork Tree, 2%; Angelicae Dahuricae Root, 1%; Lemon, 3%; Smartweed, 2%; Licorice, 0.5%; Cnidii Rhizoma, 0.5%; Japanese *Angelica* Root, 0.5%; salicylic acid, 0.5%; resorcinol, 0.5%; alcohol, 30%; and water, 48.5% (claim 9).

According to the above described lotion for therapy of dermatitis, the highest therapeutic effect against atopic dermatitis can be obtained owing to the fact that very well-balanced antibacterial, antiviral, antiallergic, antiphlogistic, blood-circulation accelerating and anti-itching effects of Lightyellow Sophora Root, Turmeric, Magnolia Bark, Moutan Bark, Isatis Leaf and Borneo Camphor Tree (*Dryobalanops aromatica* Gaertn.f.) as the main extracts drawn from plants, assisting action and enhancing action for pharmacological activities by Amur Cork Tree, Angelicae Dahurikae Root, Lemon, Smartweed, Licorice and the like as the auxiliary extracts drawn from plants, skin permeating action of Cnidii Rhizoma and/or Japanese Angelicae Root, and keratinization accelerating action of salicylic acid and/or resorcinol are obtained.

The invention is also characterized in that the volume ratios of respective ingredients are Lightyellow Sophora Root, 2.7 to 3.3%; Turmeric, 1.8 to 2.2%; Magnolia Bark, 1.8 to 2.2%; Moutan Bark, 1.8 to 2.2%; Isatis Leaf, 0.9 to 1.1%; Borneo Camphor Tree (*Dryobalanops aromatics* Gaertn.f.), 0.9 to 1.1%; Amur Cork Tree, 1.8 to 2.2%; Angelicae Dahuricae Root, 0.9 to 1.1%; Lemon, 0 to 3.3%; Smartweed, 0 to 2.2%; Licorice, 0 to 0.55%; dimethylsulfoxide, 4.5 to 5.5%; salicylic acid, 0.45 to 0.55%; resorcinol, 0.45 to 0.55%; alcohol, 21 to 31%; and water, 45 to 51% (claim 10).

When respective ingredients other than alcohol and water among the above described ingredients are less than the lower limit of the above range, appearance of medical effect is slow or no medical effect appears; when it exceeds the upper limit of the above range, there is a fear that a side effect in which skin become red and swelled or the symptom become worse occurs.

According to the above described lotion for therapy of dermatitis, a high therapeutic effect against atopic dermatitis can be obtained owing to the fact that well-balanced antibacterial, antiviral, antiallergic, antiphlogistic, blood-circulation accelerating and anti-itching effects of Lightyellow Sophora Root, Turmeric, Magnolia Bark, Moutan Bark, Isatis Leaf and Borneo Camphor Tree (*Dryobalanops aromatica* Gaertn.f.) as the main extracts drawn from plants, assisting action and enhancing action for pharmacological activities by Amur Cork Tree, Angelicae Dahurikae Root, Lemon, Smartweed, Licorice and the like as the auxiliary extracts drawn from plants, skin permeating action of dimethylsulfoxide, and keratinization accelerating action of salicylic acid and/or resorcinol are obtained.

The invention is also characterized in that the volume ratios of respective ingredients are Lightyellow Sophora Root, 3%; Turmeric, 2%; Magnolia Bark, 2%; Moutan Bark, 2%; Isatis Leaf, 1%; Borneo Camphor Tree (*Dryobalanops aromatica* Gaertn.f.), 1%; Amur Cork Tree, 2%; Angelicae Dahuricae Root, 1%; Lemon, 3%; Smartweed, 2%; Licorice, 0.5%; dimethylsulfoxide, 5%; salicylic acid, 0.5%; resorcinol, 0.5%; alcohol, 26%; and water, 48.5% (claim 11).

According to the above described lotion for therapy of dermatitis, the highest therapeutic effect against atopic dermatitis can be obtained owing to the fact that very well-balanced antibacterial, antiviral, antiallergic, antiphlogistic, blood-circulation accelerating and anti-itching effects of Lightyellow Sophora Root, Turmeric, Magnolia Bark, Moutan Bark, Isatis Leaf and Borneo Camphor Tree (*Dryobalanops aromatica* Gaertn.f.) as the main extracts drawn from plants, assisting action and enhancing action for pharmacological activities by Amur Cork Tree, Angelicae Dahurikae Root, Lemon, Smartweed, Licorice and the like as the auxiliary extracts drawn from plants, skin permeating action of dimethylsulfoxide, and keratinization accelerating action of salicylic acid and/or resorcinol are obtained.

Figure 1:
[FIG. 1]
Figure 1:
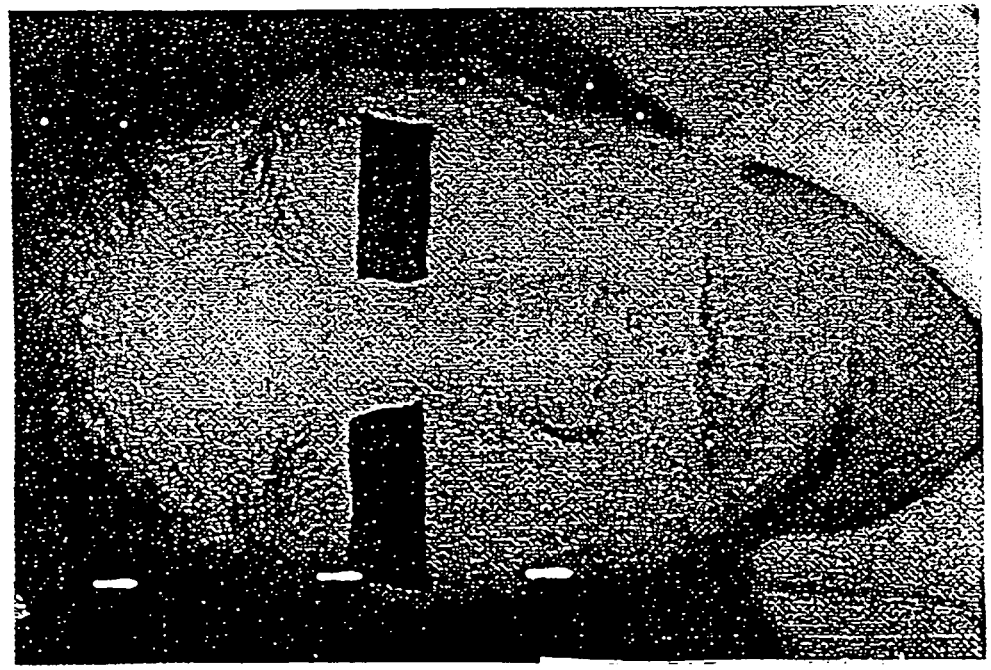

(A) is a photograph showing the face when the patient in CASE 1 according to the invention has visited a doctor for initial consultation.

(B) is a photograph showing the face after treatment.

[FIG. 2]

(A) is a photograph showing the face when the patient in CASE 2 according to the invention has visited a doctor for initial consultation.

(B) is a photograph showing the face after treatment.

[FIG. 3]

(A) is a photograph showing the backside of right hand when the patient in CASE 2 according to the invention has visited a doctor for initial consultation.

(B) is a photograph showing the backside of right hand after treatment.

[FIG. 4]

(A) is a photograph showing the face when the patient in CASE 3 according to the invention has visited a doctor for initial consultation.

(B) is a photograph showing the face after treatment.

[FIG. 5]

(A) is a photograph showing the fingers of right hand when the patient in CASE 4 according to the invention has visited a doctor for initial consultation (B) is a photograph showing the fingers of right hand after treatment.

[FIG. 6]

(A) is a photograph showing the sole of right foot when the patient in CASE 5 according to the invention has visited a doctor for initial consultation.

(B) is a photograph showing the sole of right foot after treatment.

[FIG. 7]

(A) is a photograph showing the face when the patient in CASE 6 according to the invention has visited a doctor for initial consultation.

(B) is a photograph showing the face after treatment.

BEST MODE FOR CARRYING OUT THE INVENTION

The respective ingredients and volume ratios of lotion A for therapy of dermatitis:

Lightyellow Sophora Root, 3%; Turmeric, 2%; Magnolia Bark, 2%; Moutan Bark, 2%; Isatis Leaf, 1%; Borneo Camphor Tree (*Dryobalanops aromatica* Gaertn.f.), 1%; Amur Cork Tree, 2%; Angelicae Dahuricae Root, 1%; Lemon, 3%; Smartweed, 2%; Licorice, 0.5%; Cnidii Rhizoma, 0.5%; Japanese *Angelica* Root, 0.5%; salicylic acid, 0.5%; resorcinol, 0.5%; alcohol, 30%; water, 48.5%.

The respective ingredients and volume ratios of lotion B for therapy of dermatitis:

Lightyellow Sophora Root, 3%; Turmeric, 2%; Magnolia Bark, 2%; Moutan Bark, 2%; Isatis Leaf, 1%; Borneo Camphor Tree (*Dryobalanops aromatica* Gaertn.f.), 1%; Amur Cork Tree, 2%; Angelicae Dahuricae Root, 1%; Lemon, 3%; Smartweed, 2%; Licorice, 0.5%; dimethylsulfoxide, 5%; salicylic acid, 0.5%; resorcinol, 0.5%; alcohol, 26%; water, 48.5%.

As a result of applying the above described lotion (A, B) for therapy of dermatitis onto a diseased part of a patient having atopic dermatitis, the following therapeutic results were obtained. In addition, a significant therapeutic effect can be obtained by application of the lotion (atopic lotion) (A, B) alone for therapy of dermatitis onto the diseased part; however, a more significant effect could be obtained by drinking a tea for therapy of dermatitis (atopic tea), described below, and concomitantly applying a cream (atopic cream) (A, B) for therapy of dermatitis, described below, developed by the applicant onto the diseased part. In the following CASEs, the 3 times a day applying of the atopic lotion (A, B) and the atopic cream (A, B) and the drinking of 3 g of the atopic tea were respectively carried out at morning, noon and night.

The respective ingredients and weight ratios in the tea for therapy of dermatitis (atopic tea):

The weights of extract ingredients drawn from respective medical herbs per g of a drinkable tea in the form of powders or granules are: Lightyellow Sophora Root, 0.1 g; Isatis Leaf, 0.1 g; Terminalia Fruit, 0.02 g; Japanese *Angelica* Root, 0.05 g; Oldenlandia diffusa, 0.1 g; Smilax Glabra, 0.12 g; Dried Tangerine Peel, 0.05 g; Wild Chrysanthemum Flower, 0.1 g; Corydalis, 0.02 g; Peppermint, 0.01 g; Baikal Skullcap, 0.05 g; Lithospermum, 0.1 g; Kudingcha, 0.05 g; Smartweed, 0.1 g; and Licorice, 0.03 g.

The respective ingredients and volume ratios in the cream for therapy of dermatitis (atopic cream) A:

Lightyellow Sophora Root, 3%; Turmeric, 2%; Magnolia Bark, 2%; Moutan Bark, 2%; Isatis Leaf, 1%; Borneo Camphor Tree (*Dryobalanops aromatica* Gaertn.f.), 1%; Baikal Skullcap, 2%; Amur Cork Tree, 2%; Angelicae Dahuricae Root, 1%; Lemon, 3%; Smartweed, 2%; Licorice, 0.5%; Cnidii Rhizoma, 0.5%; Japanese *Angelica* Root, 0.5%; salicylic acid, 0.5%; resorcinol, 0.5%; mutton oil, 3%; alcohol, 3%; white soft paraffin, 70.5%.

The respective ingredients and volume ratios in the cream for therapy of dermatitis (atopic cream) B:

Lightyellow Sophora Root, 3%; Turmeric, 2%; Magnolia Bark, 2%; Moutan Bark, 2%; Isatis Leaf, 1%; Borneo Camphor Tree (*Dryobalanops aromatica* Gaertn.f.), 1%; Baikal Skullcap, 2%; Amur Cork Tree, 2%; Angelicae Dahuricae Root, 1%; Lemon, 3%; Smartweed, 1%; Licorice, 0.5%; dimethylsulfoxide, 5%; salicylic acid, 0.5%; resorcinol, 0.5%; mutton oil, 3%; alcohol, 3%; white soft paraffin, 66.5%.

[CASE 1]

Patient Distinction of Sex: Female
Date of birth: Oct. 30, 1986 (Showa 61)
Age at initial consultation: 12 years old
Initial consultation: Aug. 31, 1998 (Heisei 10)
Medical history: Onset of atopy was after birth and accompanied by asthma; Gradual aggravation from elementary school girl. No improvement was observed after use of steroidal agent.
Physical examination: Face is reddish and swollen with significant exfoliation of skin; skin of total body is rough with eczema and burn. Lichenification was found locally and there is a strong itching.
Prescription: External: Application of 3 times a day of atopic lotion A and atopic cream A on the diseased part.
Consequence: After 3 months, the symptom was significantly improved. Afterwards, only the drinking of the atopic tea was continued, and the course is in good order.
FIG. 1 (A) is a photograph showing the condition of the face at the initial consultation; FIG. 1 (B) is a photograph showing the condition of the face when 3 months were passed after starting the treatment.

[CASE 2]

Figure 2:
Figure 2:
Figure 3:
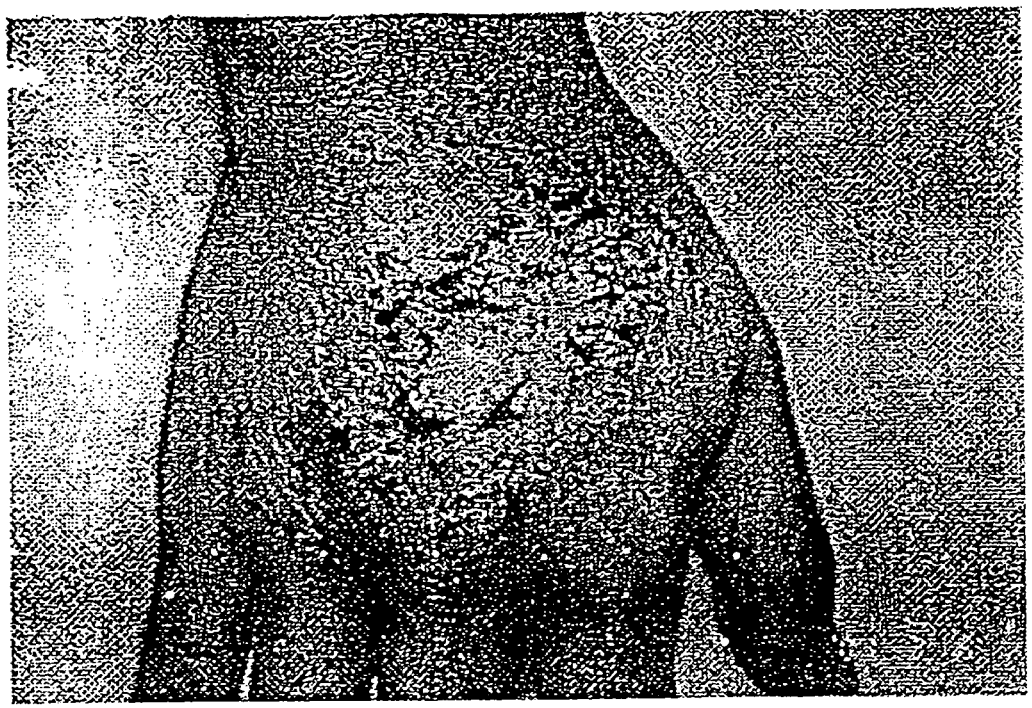
Figure 3:

Patient Distinction of sex: Female
Date of birth: Jan. 7, 1975 (Showa 50)
Age at initial consultation: 23 years old
Initial consultation: Mar. 8, 2001 (Heisei 13)
Medical history: Onset of atopy was at about elementary school girl age. No improvement was observed on use of steroidal agent Two years ago, aggravation was found after delivery; exanthema and flare were found on all of face, extremities and trunk.
Physical examination: Exanthema, flare, regional erosion, strong itch and burn were found on face. Skin of both hands is reddish, tumefacient and cracked. Lichenification was found locally.
Prescription: External: Application of 3 times a day of atopic lotion A and atopic cream A on the diseased part.
Internal: Drinking of 3 g per day of the atopic tea.
Consequence: After 3 weeks, eczema, flare, erosion, cracking and so on were almost completely cured; significant improvement of itching was found.
FIG. 2 (A) is a photograph showing the condition of the face at the initial consultation; FIG. 2 (B) is a photograph showing the condition of the face on day 13 after the treatment. FIG. 3 (A) is a photograph showing the condition of the backside of right hand at the initial consultation; FIG. 3 (B) is a photograph showing the condition of the backside of right hand on day 20 after the treatment.

[CASE 3]

Patient Distinction of sex: Male
Date of birth: Mar. 15, 1999 (Heisei 11)
Age at initial consultation: 0 year old (24 days after birth)

Figure 4:
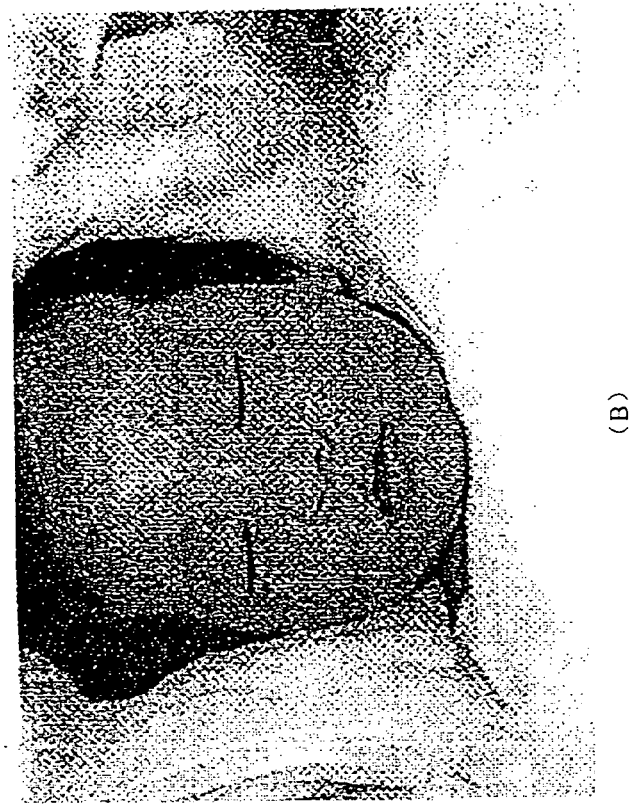
Figure 4:
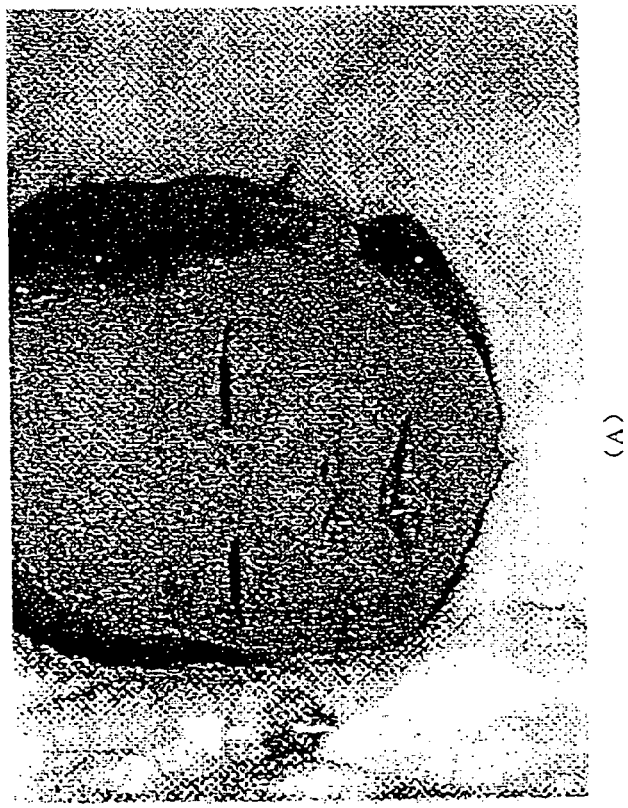

Initial consultation: Apr. 8, 1999 (Heisei 11)
Medical history: Onset of eczema was 2 weeks after birth on face as main part, head, neck and round, ears, trunk and others. No improvement was observed after use of commercially available agent. Physical examination: Eczema, exanthema and swelling on face, head, neck and round; regional pus.
Prescription: External: Application of 3 times a day of atopic lotion B and atopic cream B on the diseased part.
Internal: Drinking of 3 g per day of the atopic tea.
Consequence: After 2 weeks, the skin manifestation was significantly improved, and 2 months later, the symptoms were settled and the treatment was discontinued.
FIG. 4 (A) is a photograph showing the condition of the face at the initial consultation; FIG. 4 (B) is a photograph showing the condition of the face after 2 months.

Figure 5:
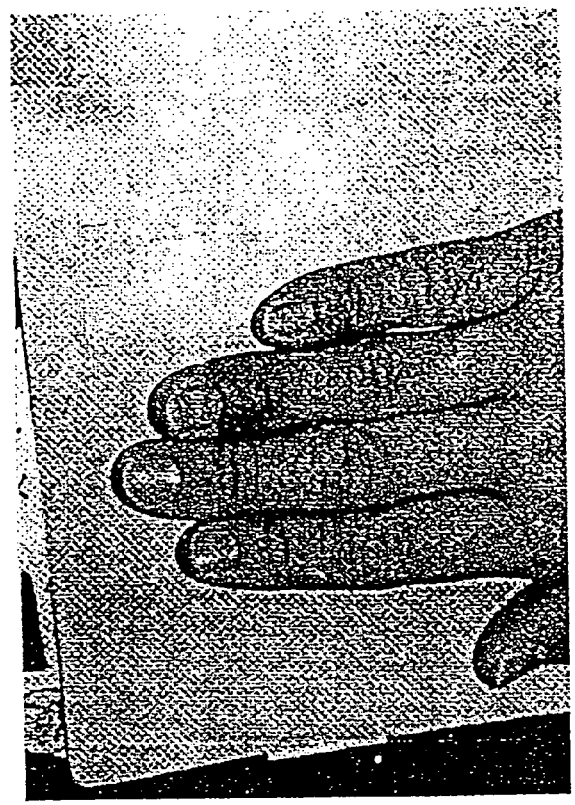
Figure 5:

[CASE 4]
Patient Distinction of sex: Male
  Date of birth: Jan. 21, 1976 (Showa 51)
  Age at initial consultation: 22 years old
Initial consultation: Dec. 11, 1998 (Heisei 10)
Medical history: Onset of atopy was at middle school boy age; gradual aggravation occurred during university student age; no improvement was observed by use of steroidal agent.
Physical examination: Flare and eczema on face and head; dry and rough. Severe eczema on both hands; strong erosion, pus, itching and burn.
Prescription: External: Application of 3 times a day of atopic lotion B and atopic cream B on the diseased part.
Internal: Drinking of 3 g per day of the atopic tea.
Consequence: After 3 weeks, eczema on both hands was almost completely cured. Improving effect was observed in symptoms on face and head.
FIG. 5 (A) is a photograph showing the condition of the fingers of right hand at the initial consultation; FIG. 5 (B) is a photograph showing the condition of the fingers of right hand after 3 weeks.

Figure 6:
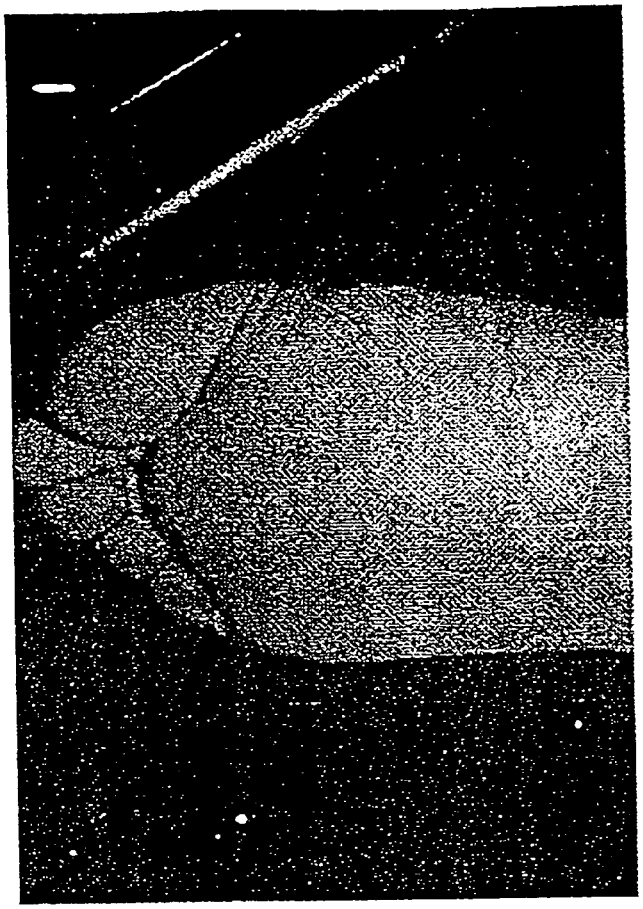
Figure 6:
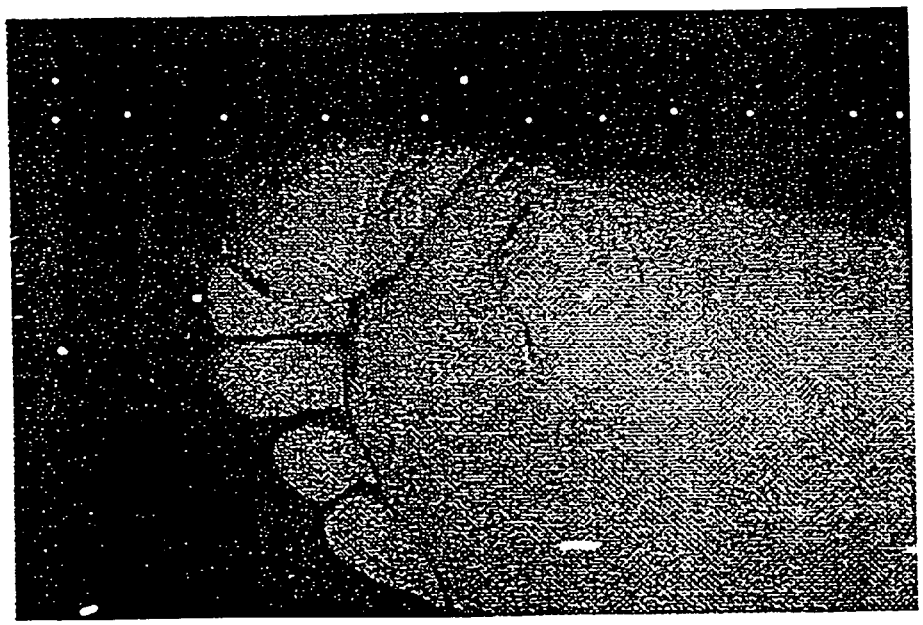

[CASE 5]
Patient Distinction of sex: Female
  Date of birth: Jun. 12, 1984 (Showa 59)
  Age at initial consultation: 14 years old
Initial consultation: Dec. 20, 1998 (Heisei 10)
Medical history: Onset of atopy was at infancy. One year ago, aggravation occurred and onset was found on all of face, trunk and extremities; erosion and pus were found. Particularly, exanthema on gluteal region and both lower limb was severe and there is a strong itching and burn.
Crack on the sole of right foot was found.
Prescription: External: Application of 3 times a day of atopic lotion A and atopic cream B on the diseased part.
Internal: Drinking of 3 g per day of the atopic tea.
Consequence: After 2 weeks, improvement of symptoms was found.
Crack on the sole of right foot was completely cured. Afterwards, only the drinking of the atopic tea was continued, and the course is in good order.
FIG. 6 (A) is a photograph showing the condition of the sole of right foot at the initial consultation; FIG. 6 (B) is a photograph showing the condition of the sole of right foot after 2 weeks.

Figure 7:
Figure 7:
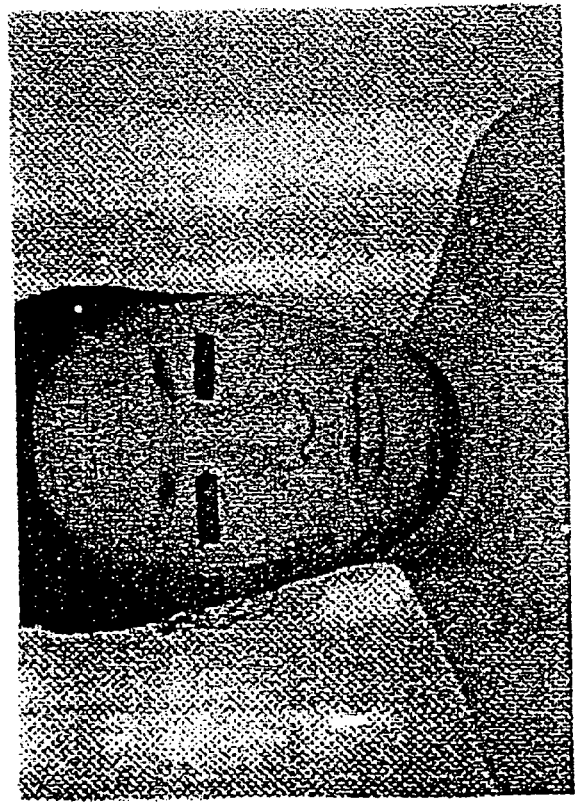

[CASE 6]
Patient Distinction of sex: Male
  Date of birth: Dec. 11, 1980 (Showa 55)
  Age at initial consultation: 20 years old Initial consultation: Apr. 1, 1999 (Heisei 11)
Medical history: Onset of atopy was after birth; steroid therapy was attempted at elementary to middle school boy age but no effect was found and the therapy was discontinued. Thereafter, antihistaminic agent alone was taken.
Physical examination: exanthema, dark redness and pigmentation on face; red swelling on neck, trunk and joints in extremities; many exfoliation; lichenification was found locally; itching is strong.
Prescription: External: Application of 3 times a day of atopic lotion B and atopic cream A on the diseased part.
Internal: Drinking of 3 g per day of the atopic tea.
Consequence: After 2 months, eczema, dark redness and pigmentation on face were almost completely cured. Eczema on trunk and extremities were significantly improved and the course afterwards is in good order.
FIG. 7 (A) is a photograph showing the condition of the face at the initial consultation; FIG. 7 (B) is a photograph showing the condition of the face after 2 months.

Besides, although description relates to cases wherein the accelerating agent for skin permeation consisting of Cnidii Rhizoma plus Japanese Angelicae Root was used in the lotion A for therapy of dermatitis and cases wherein the accelerating agent for skin permeation consisting of dimethylsulfoxide was used in the lotion B for therapy of dermatitis, similarly significant effects could be obtained in cases wherein the accelerating agent for skin permeation consisting of Cnidii Rhizoma or Japanese Angelicae Root alone was used, cases wherein the accelerating agent for skin permeation consisting of Cnidii Rhizoma plus dimethylsulfoxide was used, cases wherein the accelerating agent for skin permeation consisting of Japanese Angelicae Root plus dimethylsulfoxide was used, and cases wherein the accelerating agent for skin permeation consisting of Cnidii Rhizoma plus Japanese Angelicae Root plus dimethylsulfoxide was used.

As described above, the lotion for therapy of dermatitis according to the invention does not coat the surface of diseased part as compared with the ointment medicines, no delay of therapeutic effects by sweating action or no aggravation occurs; sufficient therapeutic effects are obtainable by only application of the lotion for therapy of dermatitis, and more significant therapeutic effects can be obtained by concomitant use with drinking of atopic tea or applying of atopic cream and the like in the initial stage of the therapy or during the total therapeutic period.

The invention claimed is:

1. A lotion for therapy of dermatitis comprising in percent by volume Lightyellow Sophora Root extract 2.7 to 3.3%; Turmeric extract, 1.8 to 2.2%; Magnolia Bark extract, 1.8 to 3.3%; Moutan Bark extract, 1.8 to 3.3%; Isatis Leaf extract, 0.9 to 1.1%; Borneo Camphor Tree extract (*Dryobalanops aromatica* Gaertn.f.), 0.9 to 1.1%; Amur Cork Tree extract, 1.8 to 2.2%; Angelicae Dahuricae Root extract, 0.9 to 1.1%; Lemon extract, 0 to 3.3%; Smartweed extract, 0 to 2.2%; Licorice extract, 0 to 1%; Cnidii Rhizoma extract, 0.45 to 0.55%; Japanese *Angelica* Root extract, 0 to 0.55%; salicylic acid, 0.45 to 0.55%; resorcinol, 0.45 to 0.55%; alcohol, 25 to 35%; and water, 45 to 51%.

2. A lotion for therapy of dermatitis comprising in percent by volume Lightyellow Sophora Root extract, 3%; Turmeric extract, 2%; Magnolia Bark extract, 2%; Moutan Bark extract, 2%; Isatis Leaf extract, 1%; Borneo Camphor Tree extract (*Dryobalanops aromatica* Gaertn.f.), 1%; Amur Cork Tree extract 2%; Angelicae Dahuricae Root extract, 1%; Lemon extract, 3%; Smartweed extract, 2%; Licorice extract, 0.5%; Cnidii Rhizoma extract, 0.5%; Japanese Angelica Root extract, 0.5%; salicylic acid, 0.5%; resorcinol, 0.5%; alcohol, 30%; and water, 48.5%.

3. A lotion for therapy of dermatitis comprising in percent by volume Lightyellow Sophora Root extract, 2.7 to 3.3%; Turmeric extract, 1.8 to 2.2%; Magnolia Bark extract, 1.8 to 2.2%; Moutan Bark extract, 1.8 to 2.2%; Isatis Leaf extract, 0.9 to 1.1 Borneo Camphor Tree extract (*Dryobalanops aromatica* Gaertn.f.), 0.9 to 1.1%; Amur Cork Tree extract, 1.8 to 2.2%; Angelicae Dahuricae Root extract, 0.9 to 1.1%; Lemon extract, 0 to 3.3%; Smartweed extract, 0 to 2.2%; Licorice extract, 0 to 0.55%; dimethylsulfoxide, 4.5 to 5.5%; salicylic acid, 0.45 to 0.55%; resorcinol, 0.45 to 0.55%; alcohol, 21 to 31%; and water, 45 to 51%.

4. A lotion for therapy of dermatitis comprising in percent by volume Lightyellow Sophora Root extract, 3%; Turmeric extract, 2%; Magnolia Bark extract, 2%; Moutan Bark extract, 2%; Isatis Leaf extract, 1%; Borneo Camphor Tree extract (*Dryobalanops aromatica* Gaertn.f.), 1%; Amur Cork Tree extract, 2%; Angelicae Dahuricae Root extract, 1%; Lemon extract, 3%; Smartweed extract, 2%; Licorice extract, 0.5%; dimethylsulfoxide, 5%; salicylic acid, 0.5%; resorcinol, 0.5%; alcohol, 26%; and water, 48.5%.

* * * * *